United States Patent [19]

Evans et al.

[11] Patent Number: 4,818,699
[45] Date of Patent: Apr. 4, 1989

[54] GENERATION OF SOMACLONAL NON-MENDELIAN VARIANTS

[75] Inventors: David A. Evans; Christopher E. Flick, both of Burlington; William R. Sharp, Camden, all of N.J.

[73] Assignee: DNA Plant Technology Corporation, Cinnaminson, N.J.

[21] Appl. No.: 525,092

[22] Filed: Aug. 22, 1983

[51] Int. Cl.$^4$ .................. C12N 5/00; C12N 15/00
[52] U.S. Cl. .................. 435/240.49; 435/172.1; 435/240.51; 435/240.54
[58] Field of Search .................. 47/58; 435/240, 241, 435/317, 172.1, 240.49, 240.51, 240.54

[56] References Cited

U.S. PATENT DOCUMENTS 4,003,156 1/1977 Sibi et al. .................. 47/58

OTHER PUBLICATIONS

Conger (Editor) 1981. *Cloning Agricultural Plants via In Vitro Techniques*, CRC Press, Inc., Boca Raton, pp. 152–153, 196–197, 142–144.
Paterson et al 1982, "Detection of Altered Inhibition of Photosystem II Reactions in Herbicide Resistant Plants" in *Methods in Chloroplast Molecular Biology*, Edelman et al eds., Elsevier Biomedical, NY, pp. 109–118.
Libbenga et al. 1973, Hormone–Induced Endoreplication Prior to Mitosis in Cultured Pea Root Cortex Cells, Am. J. Bot 60(4): 293–299.
Tran Thanh Van et al. 1978, "Plant Propagation: Non–Identical and Identical Copies" in *Propagation of Higher Plants Through Tissue Culture*, pp. 134:150–158.
Maliga et al. 1973. "Streptomycin–Resistant Plants from Callus Culture of Haploid Tobacco," *Nature New Biol.* 244:29–30.
D'Amato et al., 1980, "Nuclear Fragmentation Followed by Mitosis As Mechanism for Wide Chromosome Number Variation . . . " *Plant Cell Cultures: Results and Perspectives*, pp. 67–72.
Meredith et al, 1978, "Genetic Variation in Cultured Plants" in *Propagation of Higher Plants through Tissue Culture*, pp. 134:150–158, 166–176.
Bayliss 1973 Origin of Chromosome Number Variation in Cultured Plant Cells, Nature, vol. 246, pp. 529–530.
Galun et al 1983, "Cytoplasmic Hybridization: Genetic and Breeding Applications", in *Handbook of Plant Cell Culture VI*, Evans et al, Ed. pp. 358, 364–365.
Pring et al 1981, "Cytoplasmic Genome Variability in Tissue Cultured Derived Plants" *Env. Exp. Bot.*, vol. 21 (3/4), 369–377.
Gengenbach et al 1977, "Inheritance of Selected Pathotoxin Resistance in Maize Plants Regenerated from Cell Cultures", DNAS, vol. 74, 5113–5117.
Boxus et al 1984, "Strawberry" in *Handbook of Plant Cell Culture*, vol. 3, Ammirato et al, Eds. Macmillan Publ. Co., pp. 453, 480–481.
Ahloowalia 1984, "Forage Grasses" in *Handbook of Plant Cell Culture*, vol. 3, Ammirato et al, Eds. Macmillan Publ. Co., pp. 91, 111.
Chaleff, R. S., "Isolation of Agronomically Useful Mutants from Plant Cell Cultures", *Science* 219:676–682 (1983).
Evans, D. A. and W. R. Sharp, "Single Gene Mutations in Tomato Plants Regenerated from Tissue Culture", *Science* 221:949–951 (1983).
Orton, T. J., "Experimental Approaches to the Study of Somaclonal Variation", *Plant Molecular Biol. Reporter*, 1:2 66–76 (1983).
Reisch, B., "Genetic Variability in Regenerated Plants" In: Handbook of Plant Cell Culture, D. A. Evans, et al. Eds., Macmillian Pub., New York (1983), Chap. 25, pp. 748–469.
Sharp, W. R., D. A. Evans and P. V. Ammirato, "Plant Genetic Engineering: Designing Crops to Meet Food Industry Specifications", *Food Technology*, Feb. 1984, pp. 112–119.

Primary Examiner—Charles F. Warren
Assistant Examiner—David T. Fox
Attorney, Agent, or Firm—Pennie & Edmonds

[57] ABSTRACT

A method is presented which permits the induction and screening of variant plants which display a Non-Mendelian mode of inheritance. The process involves maintaining plant tissue in culture for a limited period of time in the presence of unusually high levels of growth regulators and screening regenerated plants recovered therefrom.

4 Claims, 2 Drawing Sheets

GENERATION OF SOMACLONAL NON-MENDELIAN VARIANTS

FIELD OF THE INVENTION

This invention relates to production of genetic variation in plants. More particularly, the subject invention relates to a method for the production and identification of variants, displaying a non-Mendelian mode of inheritance, obtained by means of tissue culture.

BACKGROUND OF THE INVENTION

Plant breeders attempting to respond to the constant demand for new varieties of crops displaying improved agronomic characteristics, have recently benefited from several innovations derived from developments in areas of plant cell or tissue culture. For example, cellular selection procedures analogous to those traditionally employed in microbial strain improvement programs, may be applied to plant cells in culture to recover useful genetic variants, anther culture may be used to decrease time necessary to achieve homozygosity, somatic cell hybridization (e.g., protoplast fusion) techniques may be employed as a means for recombining genomes of sexually incompatible species and specific gene sequences may be introduced into plant cells in culture by recombinant DNA methodologies.

More recently, the potential of tissue culture techniques as a tool for generating variation in plants has been appreciated. The tissue culture cycle generally comprises establishing cells or tissue under defined culture conditions. Explants of cotyledons, hypocotyl, stem, leaf, shoot apex, root, young inflorescences, flower petals, petioles, ovular tissues and embryos have been employed as sources of tissue for establishing the relatively dedifferentiated state in culture. (Evans, D. A., et al., *Plant Tissue Culture*, Academic Press, pp. 45-113 (1981).) While in the dedifferentiated state the cells are allowed to proliferate, thereby expanding amounts of cellular material originally derived from the explant. Finally, plantlets are regenerated from the expanded cell population. This technique, which essentially represents a form of clonal propagation, results in plants which are expected to be genetically identical to the plant from which the explant was obtained.

Contrary to the prevailing dogma of clonal propagation which asserts that the clones should be genetically identical, variation among the regenerated plantlets was occasionally noted. These were, however, usually dismissed as "artifacts of tissue culture". Incidences of these deviations from the desired characteristics displayed by the plants, which were the source of the explants, have been reported in barley (Deambrogio, E. and Dale, P. J., *Cereal Res. Comm.*, 8:417 (1980)), *Chrysanthemum*, (Jung-Heiliger, H. and Horn, W., *Z. Pflanzezuchtg.*, 85:185 (1980)), lettuce (Sibi, M., *Ann. Amelior. Plantes*, 26:523 (1976)), maize (Green, C. E., *Hort. Sci.*, 12:7 (1977), oats (Cummings, D. P., et al., *Crop Sci.*, 16:645 (1976)), onion (Novak, F. J., *Z. Pflanzenzuchtg.*, 84:250 (1980)), *Pelargonium* (Skirvin, R. M., *Euphytica*, 27:241 (1978)), pineapple (Wakassa, K., *Jap. J. Breeding*, 29:13 (1979)), potato (Shepard, J. F., et al., *Science*, 208:17 (1980)), rape (Wenzel, G., In "The Plant Genome", (D. R. Davies & D. A. Hopwood, Eds.), pg. 185 (1980)), rice (Nishi, T., et al., *Nature*, 219:508 (1968)), sorghum (Gamborg, O. L., et al., *Plant Sci. Letts.*, 10:67 (1977)), sugarcane (Heinz, D. J. and Mee, G. W. P., *Crop Sci.*, 9:346 (1969) and *Amer. J. Botany*, 58:257 (1971)), and tobacco (Sacristan, M. D. and Melchers, G., *Mol. Gen. Genet.*, 105:317 (1969) and Burk, L. G. and Matzinger, D. F., *J. Hered.*, 67:381 (1976)).

The mere reporting of such variation did not necessarily include the recognition that the variation may provide a useful source of selectable or screenable variants for crop improvement programs. The value of such variation for crop improvement has been proffered (Larkin, P. J. and Scowcroft, W. R., *Theor. Appl. Genet.*, 60:197 (1981) and Sibi, M., et al., U.S. Pat. No. 4,003,156).

In U.S. Pat. No. 4,003,156, Sibi, et al. disclose a process for obtaining variants in plants regenerated from tissue culture by means of manipulating the "epigenetic" environment during tissue culture procedure. The process does not induce changes in the genome, does not result in variants displaying classical Mendelian-type segregation, but results in a "vigor" which may be transmitted either through a pollen parent or a seed parent. By contrast, the process of the subject invention permits the induction and recovery of variants displaying a non-Mendelian mode of inheritance and the process of the copending and cofiled U.S. patent application Ser. Nos. 525,106, 4,734,369, entitled "Tissue Culture of Lycopersicon spp." Applicants: D. A. Evans and W. R. Sharp, the contents of which are incorporated herein, permits the generation and recovery of variants displaying Mendelian inheritance.

Variability has also been found in plants regenerated from protoplasts (Shepard, J. F., *Sci. Amer.*, 246:154-6 (1982)) and protoplast fusion products, i.e., somatic hybrids. Variability in traits encoded by nuclear genes, e.g., leaf morphology and disease resistance in somatic hybrids were described by Evans, et al. (*Theor. Appl. Genet.*, 62:193-198 (1982)), following protoplast fusion and subsequent proliferation of the hybrid callus a cultural situation is present which is analogous to the regeneration of plantlets from explant tissue as outlined above. However, in addition to induction of genetic changes in the tissue culture environment, interactions between respective parental nuclear and cytoplasmic genomes increase the frequency of variation in regenerated plants.

BRIEF DESCRIPTION OF THE INVENTION

This invention relates to a process for the generation and screening of variants of sexually-reproducing plants. More specifically, the variants are of a unique class in that said variants display a non-Mendelian mode of inheritance. Certain stably inherited non-Mendelin variants are due to mutations of the cytoplasmic genome of the plant (e.g., the DNA present in the mitochondria or chloroplasts). Such variants are extremely valuable as breeding stocks due to this unique mode of inheritance; ensuring all progeny will receive the cytoplasmic determinants displayed by the maternal (i.e., seed forming) parent.

According to one embodiment of the invention, the variation is induced during an interruption in the normal morphogenetic development of the plant. The interruption is most conveniently affected by removing a portion of the plant (i.e., an explant) and subjecting said explant to a brief period of tissue culture during which time the explant tissue dedifferentiates into a less organized tissue type generally referred to as callus. After a brief period of dedifferentiated growth, during which various mutations are induced, the callus is induced to regenerated plantlets during-which period the mutations are fixed within a particular regenerating plantlet. The plantlets are then allowed to mature, self-fertilize and seeds are collected. The seeds are then germinated and transplanted to replicate field plots and variants displaying a uniformity of inheritance within a row are classified as putative cytoplasmic variants. The mode of inheritance is confirmed by genetic and molecular analysis.

According to a further embodiment, somatic cell hybrids resulting from the fusion of protoplasts are used as the source of material for tissue culture rather than an explant.

According to another embodiment, the subject invention can be described as a process for the induction of genetic variation in regenerated seed plants obtained from tissue culture, the improvement comprising the steps of (a) generating said variants comprising
  (i) culturing a callus from an explant of plant tissue or from a somatic cell hybrid on basal medium containing a variation inducing amount of growth regulator substances and regenerating shoots from said callus;
  (ii) rooting said regenerated shoots on a rooting medium to form regenerated plantlets; and,
  (iii) growing said plantlets into mature plants;
(b) screening said variants comprising
  (i) collecting seed from said regenerated plant;
  (ii) germinating and growing plants therefrom,
  (iii) transplanting said plants to replicate field plots; and,
  (iv) recovering those plants which yield progeny displaying a variant phenotype throughout a full row.

DETAILED DESCRIPTION OF THE INVENTION

Figure 1:
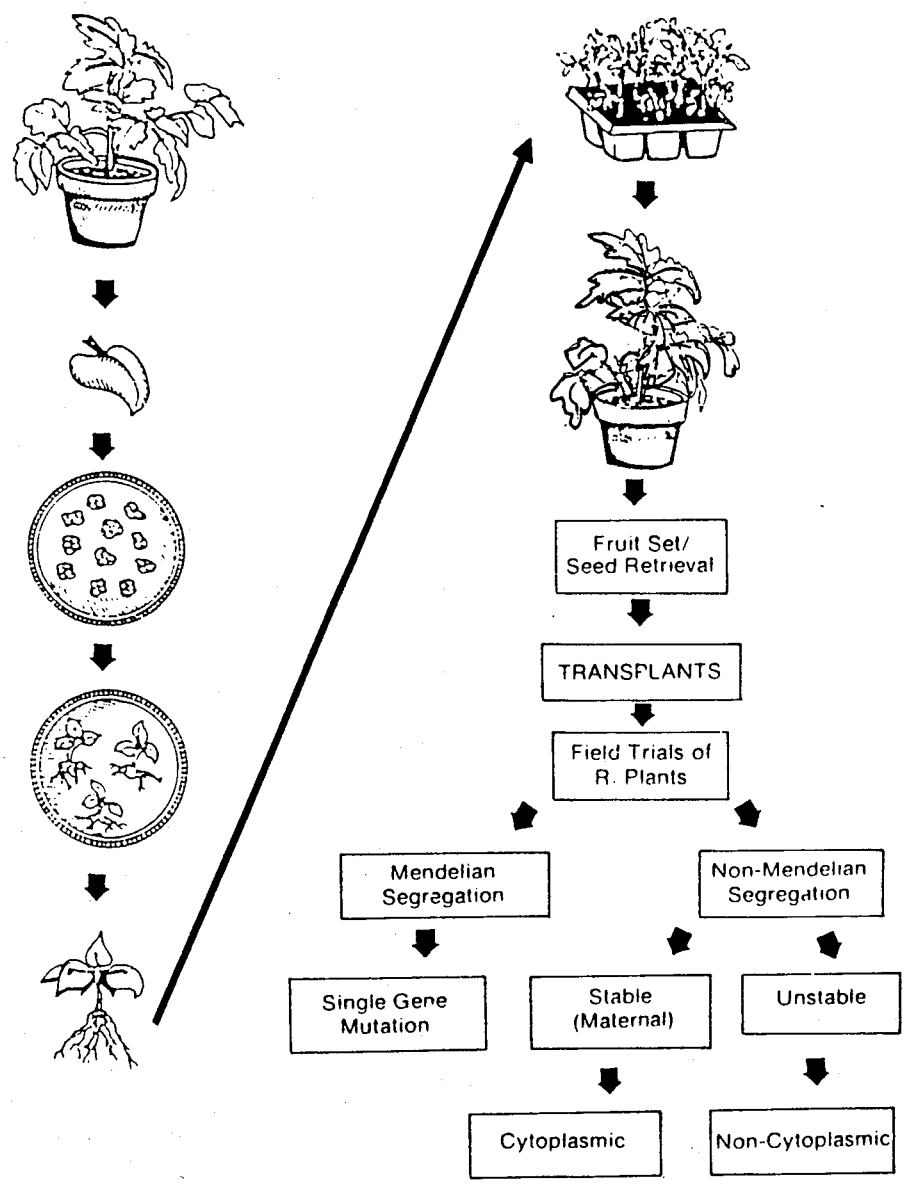
FIG. 1 is a flow scheme for generation and recovery of non-Medelian variants from plant cell cultures.

The present invention provides a method of generating and recovering new plant varieties which demonstrate a non-Mendelian mode of inheritance for a selected phenotype. The invention may be applied to a wide variety of plants, the limiting consideration being that the plant be sexually reproduced, amenable to cell or tissue culture and be regenerable therefrom. The invention may be better understood by reference to FIG. 1 and the following discussion.

The process is initiated by placing into tissue culture, an explant of tissue from the plant variety in which new variation is desired. The plant tissue is preferably sterilized prior to growing the callus. This prevents microorganisms which grow faster than the plant tissue from contaminating the culture. Methods of sterilization are known in the art. A simple and economical method is to immerse the tissue in a 7% solution of household chlorine bleach (e.g., Clorox) for about 10 minutes and then rinse the tissue two or three times with sterile distilled water. A wide variety of tissue sources are known. Explants of cotyledons, hypocotyl, stem, leaf, shoot apex, root, young inflorescenes, flower petals, petioles, ovular tissues and embryos are useful sources according to the instant invention. Although traditional mutagens such as X-rays, ultraviolet light, nitrosoguanidine and the like may be used to induce mutations which result in the desired phenotypic variation, it has been found that such mutagenic agents are not required. The present invention accomplishes the unusually variation generating step by employing growth regulators at high concentration in the basal tissue culture medium. Useful growth regulators in the context of the subject invention comprise cytokinins such as 6-benzyladenine (6-BA), kinetin, zeatin, and 2-isopentyladenine (2-iP) and auxins such as indole acetic acid (IAA), indole butyric acid (IBA), napthalene acetic acid (NAA), and 2,4- dichlorophenoxyacetic acid (2,4-D). Sterile plant tissue is then transferred to a basal medium containing 6-BA. Basal media comprise inorganic nutrients, vitamins and a carbon source. The selection of an appropriate solid basal media is within the skill of the art. Several basal media are known, including but not limited to, B5 medium, White's medium and Schenk-Hildebrandt medium. See, e.g., Gamborg, et al., (1976), *In Vitro* 12: 473-478. The preferred medium is that described by Murashige and Skoog, (1962), *Physiol. Plant.* 15: 473-497 (MS medium).

The present invention requires that 6-BA be present in the medium at a concentration of at least about 5 $\mu$M, preferably at least about 10 $\mu$M, to obtain the desired results. As noted above, the number of variant plants obtained is related to the concentration of the 6-BA. An increase in the number of variants has been observed as the 6-BA concentration was increased. It may be desirable, therefore, to increase the concentration of the 6-BA above 5 or 10 $\mu$M level. It has been found, however, that at concentrations above about 40 $\mu$M, the gain in variant plants is usually offset by a reduction in the total number of plants obtained. It is particularly preferred, therefore, to employ 6-BA in a concentration range of about 10 $\mu$M to about 40 $\mu$M. Thus, in accordance with the subject invention, plants regenerated from callus cultured on a basal medium containing high concentrations of 6-BA have shown significantly higher rates of phenotypic variation than when the cultures lacked 6-BA. The present invention, therefore, provides a method which increases the probability of recovering desirable variants by increasing the total number of variants produced.

Contrary to the teaching of Sibi, et al. U.S. Pat. No. 4,003,156 wherein a minimum of 2-3 subculturing steps prior to regeneration is preferred, it has been discovered that due to rapid accumulation of variants on 6-BA containing medium, that the time in culture should be minimized and subculturing is not necessary or desirable. The optimal exposure to tissue culture conditions will, of course, vary from one plant species to another, however, the determination of time can be ascertained by one skilled in the art based on the criteria that too short exposure will not result in a large number of variants, whilst too long exposure will cause such a large number of deleterious mutations to accumulate that the number of regenerable plantlets will be reduced to an insufficient level for screening purposes.

Following the period of undifferentiated growth, the cultures are induced to regenerate. This regeneration may be initiated by transferring the callus to a medium containing the appropriate hormones and growth regulators to permit regeneration.

It is preferred that certain growth regulators, such as indole acetic acid (IAA) be included along with the 6-BA in the basal tissue culture medium. The growth regulator (IAA), fosters partial regeneration (i.e., shoot formation) thereby limiting the duration of undifferentiated growth and thus avoiding the problems associated with the accumulation of too many undesirable mutations in the plantlet progeny as discussed above. The preferred concentration range of IAA may be employed and such variations are readily within the skill of the art. Generally, however, IAA is employed at concentrations above 1 $\mu$M and below 20 $\mu$M. Following shoot formation, the entire callus can be transferred to a rooting medium or divided so that only a portion of the callus containing shoots are transferred to the rooting medium. Once the regenerated plantlets have formed roots they may be transferred to pots and grown to mature plants. Seeds can be collected from the regenerated plants, and progeny plants arising therefrom may be screened.

The preferred rooting medium is that described for tobacco plants in Evans, et al., (1980), *Physiol. Plant.*, 48:225-230. The disclosed medium is one-half strength MS medium containing 3-aminopyridine. Although not required, it is particularly preferred to add napthylene acetic acid (NAA). Employing NAA increases the number of successfully rooted plants. The chance of losing a desirable variant because of the failure of a shoot to form roots, therefore, is reduced. The preferred concentration of 3-aminopyridine in the rooting media is about 74 $\mu$M and for the NAA is about 2 $\mu$M. Variations of the preferred rooting media are readily within the skill of the art.

Preferably, the screening involves sowing the seeds from the regenerated plants (R) in the greenhouse and transplanting the progeny ($R_1$ plants) to the field in replicated field plots. Morphological variants are identified in the greenhouse prior to transplanting and in the field as the $R_1$ plants reach maturity. Morphological characteristics such as large growth habit, small fruit with late plant development, altered leaf shape, dark green leaf, earliness or sterile plants comprise some of the variant phenotypes which may be observed.

The present invention is predicated on the discovery that the growth regulator-containing medium described herein may be used to generate variants which display a non-Mendelian mode of inheritance. For purposes of this discussion, non-Mendelian inheritance is defined as a mode of inheritance which deviates from those progeny ratios (i.e., 3:1 or 1:2:1) which are indicative of the segregation of single nuclear genes. Classically, non-mendelian inheritance has been equated with cytoplasmic or maternal transmission of genetic traits, that is to say, by means of heritable changes in the genetic information of chloroplasts or mitochondria. This mode is characterized by a uniformity of inheritance whereby the subject trait is transmitted by the parent (normally maternal) that contributes the cytoplasm at fertilization. More recently, a less stable form of non-Mendelian inheritance has been observed whereby genetic determinants, carried by moveable genetic elements, are transmitted from generation to generation. These elements may be located within the cytoplasm or nucleus but regardless of their specific location will result in a progeny ratio inconsistent with the inheritance displayed by stably transmitted single nuclear genes. Both these forms of non-Mendelian inheritance are contemplated by the subject invention.

It was completely unexpected that, for example, a stably inherited cytoplasmic mutation would be generated and recoverable from tissue culture. This belief was due in large part to the knowledge that very few cytoplasmic mutants have been isolated following conventional mutagenesis. This is due to the large population (in excess of 50 chloroplasts per mesophyll cell (Possingham, J. V., *Annl. Re. Plant. Phys.*, 31:113-29 (1980)) of chloroplasts and several hundred mitochondria per cell present during normal plant growth. Thus, any variation resulting from the alteration of the genome of a single chloroplast or mitochondria will have a small possibility of fixation in the population. According to mathematical probabilities, sorting out of novel organelle types should near completion in 10n generations where n is one-half the organelle number (Kirk and Tilney-Bassett, In: *The Plastids* W. H. Freeman, New York, pp. 218, 1967). In other words, it is estimated that 250 cell generations are needed to produce a true-breeding cell line with a single novel organelle type.

Thus even if a mutation occurred in a chloroplast, a rare event, in and of itself; the fact that the mutant bearing chloroplast is in a common cytoplasm with approximately 49 other non-mutant chloroplasts, dramatically increases the odds of ever recovering a plant which contains only mutant chloroplasts.

However, according to the invention disclosed herein, applicants provide a process which permits the induction and recovery of plants expressing said stably-inherited cytoplasmic mutations.

Although not wishing to be bound by the following explanation applicants believe during the process of plant regeneration from tissue culture, according to the subject invention, at least two processes are fostered which contribute to the fixation of the variant phenotype. During the process of regeneration according to the instant invention, rapid cell growth tends to reduce the number of plastids per cell from about 50 to about 7 and of mitochondria per from several hundred to less than about 10 per cell. Thus, when practicing the subject invention, sorting out to a novel organelle type, according to the formula above, requires only 35 cell generations; thus permitting the fixation of the genetically altered type of organelle during the process of shoot regeneration. Hence, the probability of fixing a variant organelle type has been increased substantially by using the plant cell culture of this invention to induce mutations.

Furthermore, during the dedifferentiated state imposed by the tissue culture procedure, not only are the cells less differentiated but so are the chloroplasts. These less differentiated chloroplasts, known as proplastids, will not be subject to any selection pressure (for or against) until they redifferentiate into functioning chloroplasts. Thus a mutant bearing chloroplast will not be selected against prior to plant regeneration thereby increasing the likelihood of recovering a plant with a variant phenotype.

As mentioned above, the subject invention is applicable to any sexually reproducible plant which is capable of being subjected to tissue culture and is recoverable therefrom. To better illustrate the instant invention but not to limit its scope, the following examples are presented.

EXAMPLE 1

This example illustrates the generation, recovery and verification of cytoplasmically inherited variants from explants of Lycopersicon.

Seeds of a standard inbred processing tomato variety, UC82B (Stevens, et al., 1978 *Vegetable Crops Series* #183, University of California 1978), were grown and plants with uniform, normal morphology were identified as donor plants. Young, fully expanded tomato leaves were taken from the donor plants, sterilized by immersion in 7% Clorox for 10 minutes, and rinsed 2-3 times with sterile distilled water. Portions of the leaf tissue, approximately 5 cm X 5 cm, were excised from the leaf with a sterile scalpel and aseptically transferred to a jar containing MS media (Murashige and Skoog, *Physiol. Plant*, 15:473-479 (1962)) with the addition of 6-BA at a concentration of 10 μM and IAA at a concentration of 10 μM. A callus mass developed shortly and shoots were regenerated in three to four weeks.

All shoots regenerated from said callus were transferred to a rooting media comprised of one-half strength MS media with 74 μM 3-aminopyridine and 2 μM NAA. Only one to two shoots were regenerated per explant. Plantlets were recovered on rooting medium three to twelve weeks after culture initiation. Between one and three plants were recovered from each explant that regenerated shoots.

Regenerated plants (R) were transferred to a greenhouse after being placed in soil. The R plants were self-fertilized and seed was collected from each regenerated plant to evaluate the next ($R_1$) generation. Seeds for $R_1$ plants were sown in the greenhouse and were transplanted to replicated field plots to evaluate genetic variability. $R_1$ seeds of over 500 regenerated plants were evaluated in replicated field plots. Surprisingly, several variant plants yielded seed which, upon replicated field plot testing, displayed "full row variation". This lack of segregation is suggestive of the cytoplasmic mode of inheritance and is illustrated in Table I.

Variant lines in Table I, continued to display full row variation when the progeny of $R_2$ and $R_3$ self-fertilized generations were analyzed.

TABLE 1

| | Sample Lines Observed in the Field That Behave As Cytoplasmic Traits | | |
|---|---|---|---|
| | | No. of Plants | |
| Line # | Variant Phenotype | Normal | Variant |
| 1067 | sterile plants | 0 | 45 |
| 882 | large growth habit | 0 | 45 |
| 1195 | little fruit with late plant development | 0 | 48 |
| 1941 | altered leaf shape | 0 | 48 |
| 1163 | dark green leaf | 0 | 48 |
| 1806 | earliness | 0 | 48 |

Additionally, two other variant lines displaing the same stably inherited "full row variation" (i.e., lack of segregation) were determined to affect chemical traits. Line #43 displayed a higher lycopene content than did the UC82B line, whereas Line #48 displayed a higher total solids content. Line #48 was identified in the field as distinct from the standard processing tomato, UC82B. All plants of this line in replicated field plots had increased foliage and smaller fruits than controls in the field. When evaluated in the laboratory this line contained higher total solids than the original variety.

Figure 2:
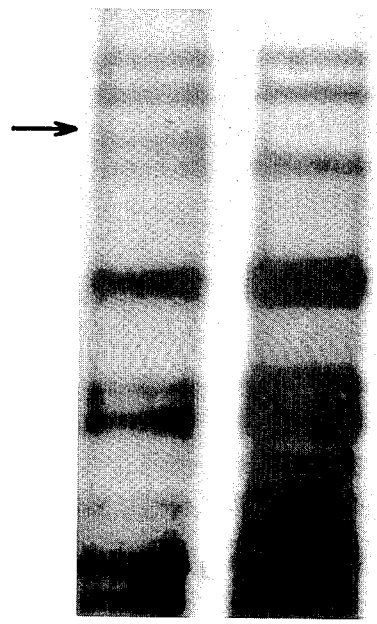
FIG. 2 is a photograph of the restriction enzyme analysis to tomato variants generated in accordance with the subject invention.

To verify the cytoplasmic nature of the genetic variation in Line #48, chloroplast DNA was subjected to restriction enzyme analysis. This technique, which is well known in the field of plant molecular biology, involved purifying chloroplasts from vegetatively growing plants by sucrose gradient centrifugation, and then extracting and purifying the DNA by CsCl-ethidium bromide centrifugation. The restriction enzyme digestion was performed according to the procedures provided by the commercial supplier. The resulting DNA fragments were separated by electrophoresis and visualized by ethidium bromide staining. FIG. 2 is a photograph of the pattern obtained from the restriction enzyme Bam Hl. Lane 1 contains the DNA fragments generated by the action of Bam Hl on UC82B-48, the high total solids variety. Lane 2 contains the DNA fragments generated by the action of Bam Hl on UC82B, the normal parent line. Lane 3 contains the digestion products of bacteriophage λ DNA by the Hind III restriction enzyme and is employed as a molecular weight standard.

Following Bam Hl digestion of UC82B-48 (Lane 1) a DNA fragment is absent (arrow) from the normal UC82B profile (Lane 2). This represents a change in the Bam Hl hexanucleotide recognition sequence in the chloroplast DNA. Digestions with other restriction enzymes, such as Sal I, Eco RI and Sma I, show no difference in digestion between the mutant and parental DNA patterns, implying a single base pair or limited deletion rather than a large rearrangement or deletion of chloroplast DNA.

EXAMPLE 2

This example illustrates the recovery of unstable variants from somatic hybrids resulting from protoplast fusion.

Whereas stably inherited cytoplasmic gene controlled variability was achieved from tissue culture of explants from whole tomato plants in Example I, variability may also be generated in plants regenerated from protoplasts and protoplast fusion products, i.e., somatic hybrids.

A single plant with a high frequency of dark green and aurea spots on the leaves was obtained following the regeneration of plants from callus derived from somatic hybridization of *Nicotiana sylvestris* and *Nicotiana tabacum* as described by Evans, et al. *Theor. Appl. Genet.*, 65:93-101 (1983), the entire content of which is incorporated herein by reference. This high frequency of spotting was inherited in one of 10 progeny of self-fertilization ($R_1$ generation), but not inherited following backcrossing to either parent. This low transmission frequency precludes control by a simple Mendelian mutation. Of 37 plants, in the next generation ($R_2$) 27 expressed the high spotting phenotype. The pattern of inheritance in the $R_1$ (low frequency of transmission) and the $R_2$ (high frequency of transmission) generations precludes control by recessive or dominant nuclear, multiple nuclear, or cytoplasmic genes. Restriction enzyme analysis showed no differences between this hybrid, *N. tabacum*, or *N. sylvestris* in banding patterns for the enzymes Xba I, Kpn I, Sal I, Sma I, Eco RI, Bam Hl, and Hind III suggesting that chloroplast DNA is not involved. The transition fom low transmission to high transmission frequency underscores the instability of this trait.

Unstable traits resulting in variegated plants with similarities to one described above have been reported in several other higher plant species. These include variation in maize kernel color (Fincham, J. R. S. and Sastry, G. R. K., *Ann. Rev. Gent.*, 8:15-50 (1974)) and Antirrhinum and Impatiens flower color (Sastry, G. R. K., et al., *Cold Spring Harbor Symp. Quant. Biol.*, 46:477-86 (1981)). In most cases, these instabilities have been explained by transposable elements. As with the segregation data herein, abnormal segregation ratios were also reported for the Antirrhinum system (Sastry, G. R. K., et al., 1981, supra). It should be noted that variation has previously been reported following interspecies sexual hybridization for other Nicotiana species. For example, flower color variation was observed in plants derived from *N. langsdorfii* x *N. sanderae* (Smith, H. A. and Sand, S. A., *Genetics*, 42:560–582 (1957)) and *N. tabacum* x *N. otophora* (Gerstel, D. C. and Burns, J. R., *Genetics*, 66:331–38 (1970)) sexual hybrids. Hence, several characteristics of the variant described herein suggest comparison to a transposon based mode of inheritance.

What is claimed is:

1. A method for isolating non-Mendelian genetic variants in regenerated tomato plants obtained from tissue culture, comprising the steps of:
   (i) culturing a callus from an explant of tomato plant tissue of basal medium comprising a variant inducing amount of cytokinin and auxin and regenerating shoots from said callus;
   (ii) rooting said regenerated shoots on a rooting medium to form regenerated plantlets;
   (iii) growing said plantlets into mature tomato plants;
   (iv) collecting seed from said regenerated plants;
   (v) germinating and growing plants therefrom;
   (vi) transplanting said plants to replicate field plots;
   (vii) isolating those plants which yield progeny displaying a variant phenotype throughout a full row and,
   (viii) verifying the cytoplasmic nature of the variation by subjecting chloroplast DNA to restriction enzyme analysis.

2. The method according to claim 1 wherein said explant is selected from the group consisting of cotyledons, hypocotyl, stem, leaf, shoot apex, root, young inflorescenes, flower petals, petioles, ovular tissue and embyros.

3. The method according to claim 1 wherein said cytokinin is selected from the group consisting of 6-benzyladenine, kinetin, zeatin and 2-isopentyladenine and said auxin is selected from the group consisting of indole acetic acid, indole butyric acid, napthalene acetic acid, and 2,4-dichlorophenoxyacetic acid.

4. The method according to claim 3 wherein said cytokinins and auxins are 6-benzyladenine and indole acetic acid.

* * * * *